United States Patent
Hamilton et al.

(10) Patent No.: US 9,063,897 B2
(45) Date of Patent: Jun. 23, 2015

(54) POLICY-BASED SECURE INFORMATION DISCLOSURE

(75) Inventors: James R. Hamilton, Bellevue, WA (US); Vladimir G. Sadovsky, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 1228 days.

(21) Appl. No.: 12/146,721

(22) Filed: Jun. 26, 2008

(65) Prior Publication Data

US 2009/0328130 A1  Dec. 31, 2009

(51) Int. Cl.
*G06F 21/00* (2013.01)
*G06F 12/14* (2006.01)
*G06F 19/00* (2011.01)
*G06F 21/62* (2013.01)
*H04L 29/06* (2006.01)

(52) U.S. Cl.
CPC .... *G06F 12/1466* (2013.01); *G06F 2221/2111* (2013.01); *G06F 21/6218* (2013.01); *G06F 2221/2141* (2013.01); *H04L 63/105* (2013.01); *G06F 19/323* (2013.01)

(58) Field of Classification Search
CPC ............... H04L 63/105; G06F 21/6218; G06F 2221/2141; G06F 19/323; G06F 2221/2111
USPC .......... 726/1, 2, 4–6, 9, 20, 27; 713/159, 171, 713/172
See application file for complete search history.

(56) References Cited

U.S. PATENT DOCUMENTS

| | | | | |
|---|---|---|---|---|
| 5,763,862 | A * | 6/1998 | Jachimowicz et al. | 235/380 |
| 5,802,494 | A * | 9/1998 | Kuno | 705/2 |
| 6,038,551 | A * | 3/2000 | Barlow et al. | 705/41 |
| 6,044,349 | A * | 3/2000 | Tolopka et al. | 705/1.1 |
| 6,306,088 | B1 | 10/2001 | Krausman et al. | |
| 6,605,046 | B1 | 8/2003 | Del Mar | |
| 6,763,463 | B1 * | 7/2004 | Guthery | 713/193 |
| 7,215,983 | B2 * | 5/2007 | Cho et al. | 600/316 |
| 7,270,633 | B1 * | 9/2007 | Goscha et al. | 600/300 |
| 7,376,839 | B2 * | 5/2008 | Carta et al. | 713/185 |
| 2003/0032991 | A1 * | 2/2003 | Poore | 607/32 |
| 2003/0114206 | A1 | 6/2003 | Timothy et al. | |
| 2004/0087839 | A1 * | 5/2004 | Raymond et al. | 600/300 |

(Continued)

OTHER PUBLICATIONS

CodeBlue: Wireless Sensor Networks for Medical Care. Last updated Sep. 26, 2006. http://www.eecs.harvard.edu/~mdw/proj/codeblue/. Last accessed Oct. 26, 2007, 4 pages.

(Continued)

*Primary Examiner* — Carl Colin
*Assistant Examiner* — Gary Lavelle
(74) *Attorney, Agent, or Firm* — Julie Kane Akhter; Danielle Johnston Holmes; Micky Minhas

(57) ABSTRACT

Systems and methods for storing data and retrieving data from a smart storage device is provided, where smart storage includes processing capabilities along with the ability to store information. In one aspect, a method includes detecting via bidirectional settings one or more capabilities of rules enforcement logic associated with a storage device and selecting a set of criteria and policies to be downloaded from a host or a management server that are to be downloaded onto the storage device. This includes dynamically generating conditional context aware policies syntax based on user settings or network policy and downloading a set of policies onto the storage device for future policy enforcement.

20 Claims, 12 Drawing Sheets

(56) References Cited

U.S. PATENT DOCUMENTS

| | | |
|---|---|---|
| 2004/0088567 A1* | 5/2004 | Lamotte ................. 713/200 |
| 2004/0122294 A1* | 6/2004 | Hatlestad et al. ............. 600/300 |
| 2004/0186746 A1 | 9/2004 | Angst et al. |
| 2006/0004974 A1 | 1/2006 | Lin et al. |
| 2006/0015368 A1 | 1/2006 | Hockey |
| 2006/0059548 A1* | 3/2006 | Hildre et al. ................. 726/9 |
| 2006/0080137 A1 | 4/2006 | Chambers et al. |
| 2006/0177061 A1* | 8/2006 | Orsini et al. ................. 380/268 |
| 2006/0202816 A1* | 9/2006 | Crump et al. ............ 340/539.12 |
| 2006/0282436 A1* | 12/2006 | Chaudhuri et al. .......... 707/100 |
| 2007/0016452 A1 | 1/2007 | Wilson |
| 2007/0057041 A1 | 3/2007 | Sarkis et al. |
| 2007/0061393 A1* | 3/2007 | Moore ................. 709/201 |
| 2007/0094489 A1 | 4/2007 | Ota et al. |
| 2007/0150315 A1* | 6/2007 | Bennett et al. ................. 705/3 |
| 2008/0022395 A1* | 1/2008 | Holtzman et al. ............. 726/19 |
| 2008/0178300 A1* | 7/2008 | Brown et al. ................. 726/29 |
| 2009/0049518 A1* | 2/2009 | Roman et al. ................. 726/1 |

OTHER PUBLICATIONS

Emil Jovanov, et al. Patient Monitoring Using Personal Area Networks of Wireless Intelligent Sensors http://www.ece.uah.edu/~jovanov/papers/rmbs01_wireless.pdf. Last accessed Oct. 26, 2007, 6 pages.

* cited by examiner

POLICY-BASED SECURE INFORMATION DISCLOSURE

BACKGROUND

Conventionally, sensitive information is stored and protected from unauthorized tampering through use of software encryption. For a party requesting access to the software-encrypted information, the party or other requesting entity typically supplies a pass phrase or digital key that determines if information release from the protected medium is appropriate. If an appropriate digital key is not provided, then access is denied; conversely, an appropriate digital key enables an entity to gain access to the information. This type of access to the protected medium is referred to as a binary access check, where entry to the storage medium is either granted or denied based upon a singular event such as producing a suitable key.

According to one convention, there can be a list of approved keys where supplying of one key is enough to gain access. If more parties are allowed access to the respective information, then more keys can be generated and added to a list of approved keys. Implementation of digital keys and/or pass phrases to allow for information access can be employed in media-based storage mediums, such as DVD (Digital Video Disc), diskettes, for example. Unfortunately, simply granting or denying access to the storage media may not be entirely suitable for modern applications that may require other criteria than keys or pass phrases to gain access to information.

SUMMARY

The following discloses a simplified summary of the specification in order to provide a basic understanding of some aspects of the specification. This summary is not an extensive overview of the specification. It is intended to neither identify key or critical elements of the specification nor delineate the scope of the specification. Its sole purpose is to disclose some concepts of the specification in a simplified form as a prelude to the more detailed description that is disclosed later.

Personal storage and data access to sensitive information is improved over binary access systems, where higher-level access policies are provided in accordance with smart storage devices to govern access or release of information retained therein. With development of complex storage units (e.g., storage units that use components other than pure memory), more advanced information access techniques can be practiced to enhance security. One form of complex storage is smart storage that can include use of a processor, memory, and persistent storage (e.g., NAND flash memory). Smart storage can enforce access policies that are more complex than binary access checks of non-smart storage, such as allowing access through use of policy. For example, a memory system on a chip can be provided to mitigate data tampering and inappropriate access, thus adding additional security to information retained in smart storage. Personal storage could also include integrated receiver to collect data from personal sensors to enhance and supplement respective access policies. For example, personal sensors could track body temperature, heart rate, location, speed, acceleration, and many other attributes or context related to a user or group. Thus, continuously collecting information can allow for a personal black box approach, where policy-based security is dynamic based upon currently detected states of the user.

In another aspect, personal storage can collect and retain data as well as support policy-based information release, where the information released can be based on a combination of user physical states detected and a provision of one or more keys as well as a biometric measurement. Thus, there can be conditional access checks to retained personal contextual data. Rather than merely performing binary access checks based upon whether or not a requestor supplies an appropriate key, smart storage can implement policy-based decisions to provide efficient yet more secure mechanisms regarding when or how personal information is disclosed.

The following description and the annexed drawings set forth certain illustrative aspects of the specification. These aspects are indicative, however, of but a few of the various ways in which the principles of the specification can be employed. Other advantages and novel features of the specification will become apparent from the following detailed description of the specification when considered in conjunction with the drawings.

DETAILED DESCRIPTION

Figure 1:
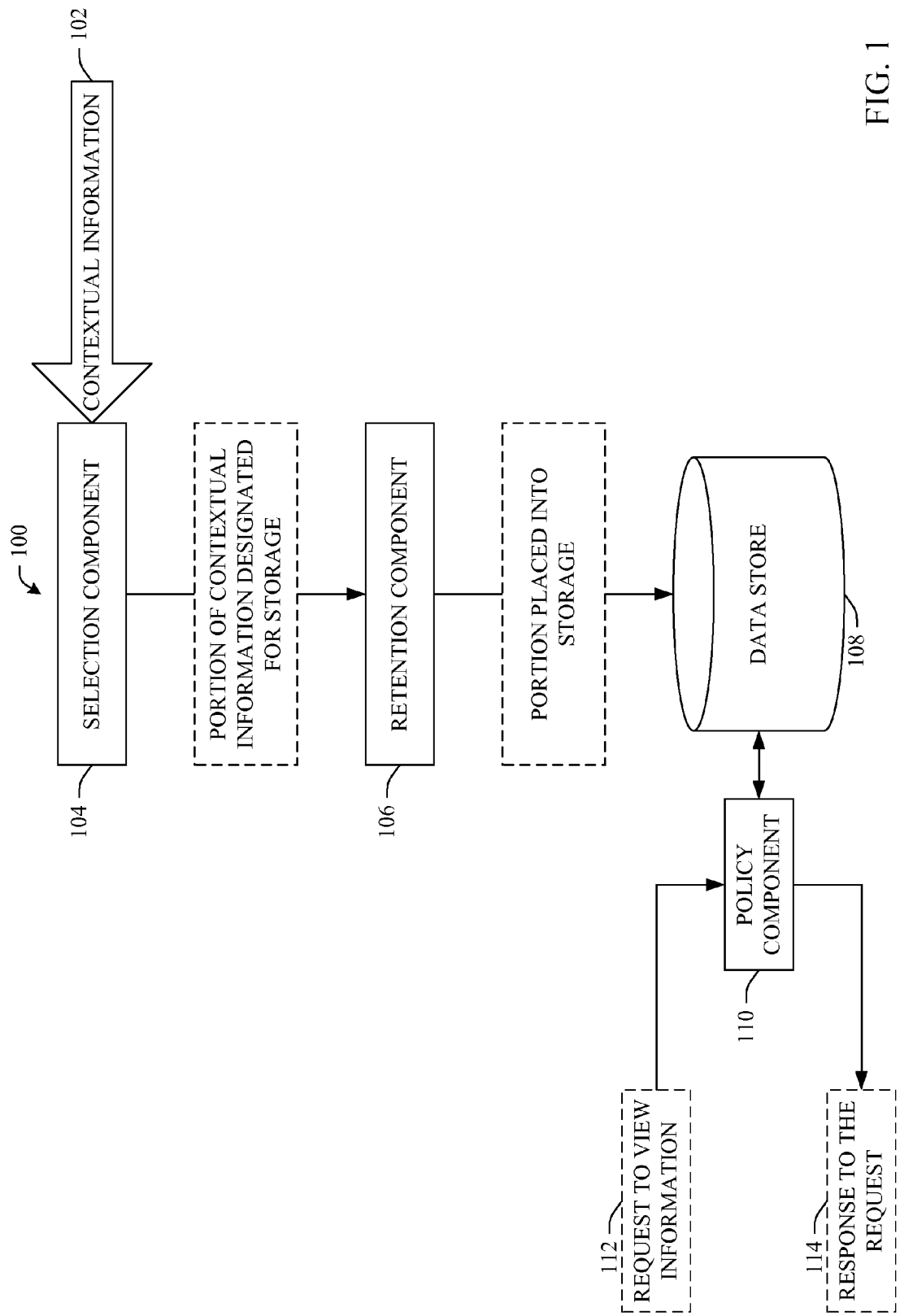
FIG. 1 illustrates a policy-based system for securely retaining information in accordance with an aspect of the subject specification.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It can be evident, however, that the claimed subject matter can be practiced without these specific details. In other instances, well-known structures and devices are shown in block diagram form in order to facilitate describing the claimed subject matter.

As used in this application, the terms "component," "module," "system," "interface," or the like are generally intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a controller and the controller can be a component. One or more components can reside within a process and/or thread of execution and a component can be localized on one computer and/or distributed between two or more computers. As another example, an interface can include I/O components as well as associated processor, application, and/or API components.

Now referring to FIG. 1, a system 100 illustrates retaining information in a secure manner and releasing the retained information through use of an access policy. Personal electronic devices can store a wide variety of information, e.g., information designated by a user, information ascertained through observation, and the like. It can be possible to aggregate this information together and perform selective storage, commonly based upon a specific theme or a desired understanding. Contextual information 102 (e.g., information that pertains to a specific topic, such as driving history). Evaluation of the contextual information 102 can occur, where a selection component 104 can determine and select contextual information for storage based upon a result of the evaluation. Selection can be specified by a person, inferred through analysis of user history, performed as a function of monetary transaction (e.g., paying a user to retain a data type), etc. A notice can transfer to a retention component 106 of information that should be stored. The retention component 106 can store and protect the selected contextual information through use of hardware-based encryption (e.g., retain the selected information upon a smartcard that functions as a data store 108).

As more contextual information 102 becomes available and is processed by the selection component 104, a continuous record can be retained relating to the individual. The retained information can focus on a certain aspect, such as medical information of the user, driving history, criminal involvement, etc. In a conventional setting, the individual can have a periodic meeting with a medical specialist, where various measurements can be taken. For example, the specialist can observe a blood pressure measurement of the individual, where a result of the observation can be interpreted as indicative of overall cardiovascular health. However, the observation can be considered a snapshot in time and thus can be influenced by extraneous factors. If the individual is under an irregular amount of stress, the result of the measurement can be higher than normal and thus incorrect treatment could be applied; which could lead to a detrimental result, such as overmedicating the individual, missing an important condition, etc.

By using the system 100, the specialist can designate that blood pressure information be retained. Random blood pressure measurements can be taken of the individual each day and safely retained upon storage in a manner that is difficult to tamper, access without authorization, and the like. The selection component 104 can determine that blood pressure information should be retained (e.g., through an inference made from a blood pressure reading being relatively high during a visit to the specialist). In addition to the measurement, other contextual information 102 can be retained that relates to the measurement. Temperature of a room, time of day, and the like can have an impact upon a result of the blood pressure measurement and thus be duly recorded. Retained information can be processed and analyzed—if a high blood pressure reading is measured while in a hot room and during a meeting with numerous attendees speaking in loud tones, then the measurement can be designated as less credible since the measurement occurs during an extreme situation.

Since a user might not want people to know about a potential blood pressure problem, the retention component 106 can safely retain the information upon the data store 108 (e.g., NAND flash memory). The data store 108 can operatively couple to a processor and/or supplemental memory and thus practice 'smart storage'. Implementation of the data store 108 can occur upon a personal electronic device of a user, such as a wristwatch, cellular telephone, portable flash memory device, and the like.

To enhance security, the system 100 can employ a policy component 110 that can allow access to information based upon a policy set. A user can program the system 100 to allow certain parties to access personal information at all times (e.g., a spouse) and allow certain parties to access information based upon at least one condition (e.g., a paramedic can obtain the information only if a user is unconscious), etc. A user can submit a request to view information 112 and the policy component 110 can determine if there should be a release based upon the policy set. The policy component 110 can submit a response to the request 114, commonly through granting access, denying access, requesting more information (e.g., such as asking the user 110 to provide identification), and the like. The request to view information 112 can originate from a user, an entity that automatically generates the request 112, and so forth. Moreover, the response to the request 114 can be returned to a requesting entity as well as transferred to a third party (e.g., a doctor requesting that a nurse be given access to information).

Additionally, release of information can be limited, such as through contextual release. If a user becomes unconscious, medical information can be disclosed to a paramedic, but not financial information such as banking pin numbers—thus information release is applicable to a certain context. Thus, policy information can be combined with a user's current state or context to release of information. While the aforementioned examples pertaining to access policies can generally be of a simple nature (e.g., singular checks), it is to be appreciated that more complex policies can be used.

In various circumstances, keys can be used in conjunction with information granting policies to determine if information release is appropriate. Access can be granted to any subset of N keys from a pool of M. For example, three children can be given authority over an elderly parent due to a medical condition of the parent. Each of the three children can be provided a distinct key—however, to access information, different configurations can be implemented. In one instance, to gain medical information related to the parent, only one child needs to present a key. However, to access financial information of the parent, at least two keys are required for access. There can also be access granted at a time that a key is presented and there is disclosure of a biometric measurement (e.g., specific fingerprint, brainwave, retinal scan etc.)

While aspects are disclosed that relate to personal contextual information, it is to be appreciated that there can be other applicability. For instance, when shipping goods, the context component 102, retention component 106, data store 108, and/or policy component 110 can be operatively coupled to a package. If the package experiences harsh treatment during shipping that could lead to damage, then a record can be made of the treatment as well as metadata related to the treatment. In one example, a package on a truck can experience rapid movement causing damage to the goods. An observation can be made that a driver went over a posted speed limit (e.g., through use of a global positioning system and speed sensor, etc.), which caused harsh movement and damage. The damage information can be retained and later extracted by a dispatcher and used to determine fault through use of an access policy set. Disclosure of the tracking information can be limited to a policy that requires access to occur at a set location, such as a truck depot, and be performed by an authorized party, such as a depot manager. This policy can be absolute (e.g., access is not granted unless the truck is in a depot and the requester is a depot manager) or lateral (e.g., either the truck is in a depot or a requester is a depot manager).

It is noted that smart storage devices that include processing capabilities along with storage capabilities can be configured and adapted for a plurality of differing applications. In one aspect, host computers can negotiate policies with the smart storage devices, digitally sign the policies, and download the signed policies to the devices where the device can then act as its own gatekeeper to grant or deny access based on the respective policies. For instance, this can include a method of placing criteria and related keys onto the smart storage device from a personal computer or similar hosting system. The method includes detecting via bidirectional settings, the respective exchange mechanism capabilities including rules enforcement logic inside the storage device. The method then selects a set of criteria and policies to be downloaded from either a host or a management server to be downloaded onto the storage device. This includes dynamically generating conditional context aware policies syntax based on user settings or network policy into a well defined grammar. After the policies have been generated, the method securely downloads the set of policies onto the smart storage devices for future enforcement.

In yet another aspect, smart devices can enable dynamic macros to enforce policies, where the macros are automatically and/or dynamically generated as conditions or context change over time. For instance, a system for creating customized executable policy rules to be executed dynamically inside a storage device before releasing access to stored data in the device can be provided. The system includes means for processing templates, where the templates are stored in a policy store on a host or enterprise network associated with a host storage management system, and where the templates are employed to create policy rules as language macros, for example. The system includes means for downloading the macros into the storage device in a secure manner (e.g., via encrypted or secure channels) and means for executing the macros when an access decision is performed by the storage device based on user keys, content metadata, or context settings, for example. A networked host can manage an attached smart storage device during provisioning, if desired.

Figure 2:
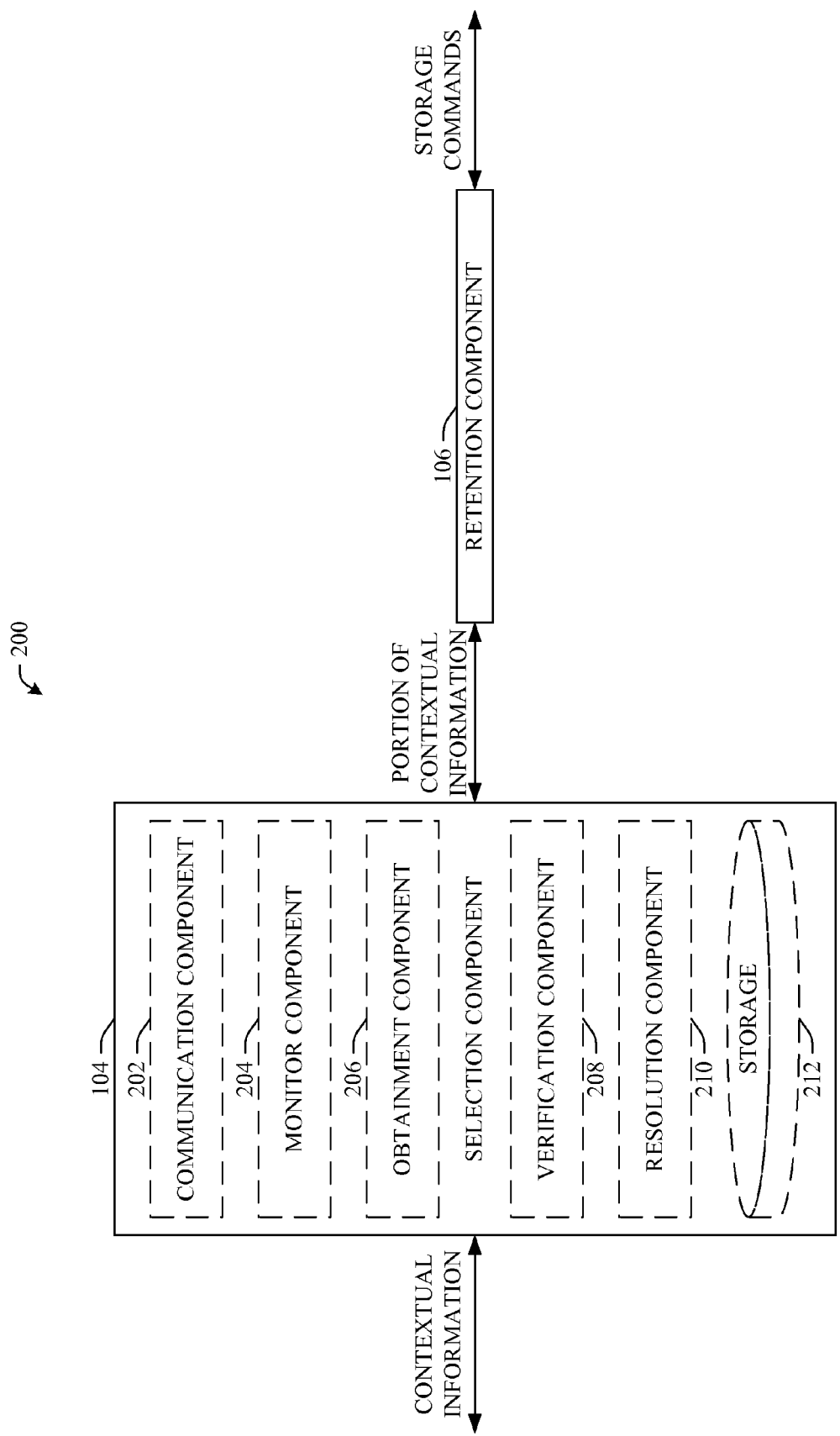
FIG. 2 illustrates a representative system for securely retaining information with a detailed retention component in accordance with an aspect of the subject specification.

Now referring to FIG. 2, an example system 200 for selectively and safely retaining information is disclosed with an example selection component 104, where saved information can be accessed through use of a policy set. The selection component 104 can process contextual information, commonly in relation to a user. Processing of the contextual information can include analyzing the information and intelligently selecting information for storage as a function of anticipated usefulness of the information. To facilitate operation, the selection component 104 can use a communication component 202 that can engage with other devices to transfer information, such as to send a request for contextual information, receiving contextual information from an auxiliary source, etc. Operation can take place wirelessly, in a hardwired manner, employment of security technology (e.g., encryption), etc. Additionally, information transfer can be active (e.g., query/response) or passive (e.g., monitoring of public communication signals). Moreover, the communication component 202 can use various protective features, such as performing a virus scan on collected metadata and blocking metadata that is positive for a virus.

Different types of contextual information can be desirable and a monitor component 204 can be employed to determine a type of information to gather. A direct request can be made by a user to gather contextual information, an observation can be made that a certain type of information could be beneficial, and the like. As conditions change, the monitor component 204 can automatically modify classifications contextual information that are gathered (e.g., add a new form of information for gathering, stop collection of information, delete records of information no longer deemed valuable, etc.). According to one aspect, the monitor component 204 can initiate sensors that perform observations, where contextual information is based upon the observations.

An obtainment component 206 can gather contextual information, where at least a portion of the gathered information can be stored. It is possible for more information to be gathered than appropriate, redundant information to be gathered, and the like. Therefore, the selection component 104 can limit gathered information that is ultimately stored. According to one aspect, the obtainment component 206 gathers contextual information of an environment (e.g., room temperature); however, the obtainment component 206 can also gather contextual information to a user response to the environment (e.g., when observing that there is a relatively high room temperature, it is noted that the user perspires).

The gathered information can be very important—in a medical context, if gathered data indicates that a user has an adverse reaction to medication, then it can be important that the information is precise. A verification component 208 can determine if gathered contextual information is accurate, where gathered contextual information can be stored if determined to be accurate and disregarded if determined to be inaccurate. In an illustrative verification, a second reading can take place if applicable and a determination can be made if a first reading and the second reading have matching answers within a tolerance.

According to one aspect, information is gathered through use of sensors. However, it is possible for sensors to produce conflicting information (e.g., originating from one sensor malfunctioning). A resolution component 210 can identify a discrepancy amongst information and can designate a portion of the gathered contextual information for storage when there is conflicting gathered contextual information. For instance, the resolution component 210 can calculate an expected value and select information that is closest to the expected value for storage, while other information is disregarded.

Different types of information, such as gathered contextual information, component operating instructions (e.g., communication component 202), components themselves, etc. can be held on storage 212. The storage 212 can be arranged in a number of different configurations, including as random access memory, battery-backed memory, hard disk, magnetic tape, etc. Various features can be implemented upon storage 212, such as compression and automatic back up (e.g., use of a Redundant Array of Independent Disks configuration). In addition, storage 212 can operate as memory that can be operatively coupled to a processor (not shown). A retention component 106 can be used that stores the selected contextual information through hardware-based encryption.

Figure 3:
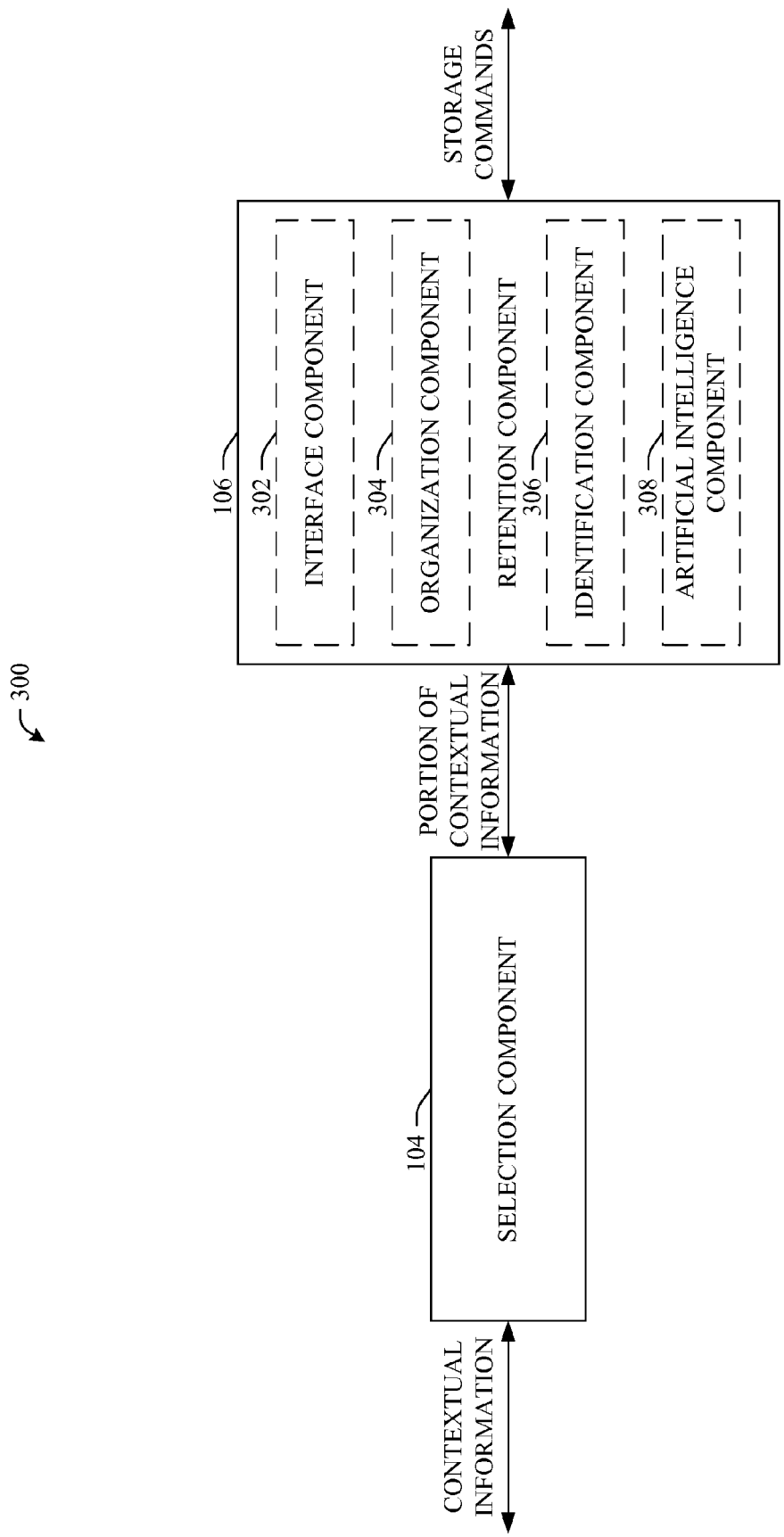
FIG. 3 illustrates a representative system for securely retaining information with a detailed security component in accordance with an aspect of the subject specification.

Now referring to FIG. 3, an example system 300 is disclosed for securely and/or selectively retaining contextual information that can be accessed through use of a policy with a detailed retention component 106. A relatively vast amount of contextual information can be collected and analyzed. Based upon a result of the analysis, a selection component 104 can select information for storage. According to one aspect, upon analysis and selection, an instruction can be generated to gather a larger amount of contextual information related to a particular topic. For instance, if through contextual information it is determined that a user has a stroke, then an instruction can be issued to refrain from collection of extraneous contextual information (e.g., room lighting) and to gather more related contextual information in a faster manner than normal (e.g., continuously monitor heart rate as opposed to periodic checks). A retention component 106 can securely store selected information, commonly through hardware encryption.

It is possible that a user desires to have personal information made available and have the information retained in a construct with the stored contextual information. An interface component 302 can facilitate an ability to gather information designated by a user for storage by the retention component 106; the interface component 302 can operate in conjunction with the obtainment component 206 of FIG. 2. In an illustrative instance, if a user desires for allergy information to be retained in addition to observed contextual information, then the user can input the allergy information through the interface component 302 and the information can be saved by the retention component 106 (e.g., inputted user information can be automatically selected by the information designation component 102). The interface component 302 can facilitate placement of a graphical user interface (GUI) upon a display to assist in gathering user information.

Since a large amount of information can be gathered and retained, an organization component 304 can be employed to manage information retention (e.g., as information is stored, after information is stored, etc.). Management can include aggregating information, deleting information as a function of time, prioritizing information, or a combination thereof. Since multiple sensors can collect multiple instances, aggregating information can allow information to be quickly processed. For example, as opposed to creating about 100 records concerning an event that takes place about 100 times, one record can be created and updated to represent that the event occurs about 100 times. If information becomes old, outdated, irrelevant, damaged, and the like, then the information can be automatically deleted by the organization component 304. However, artificial intelligence techniques can be used to protect data, such as if a user enters information, it is never automatically deleted regardless of age. In addition, artificial intelligence techniques can be used to prioritize information (e.g., create an order information is disclosed to an authenticated user).

An identification component 306 can be utilized to select an appropriate instance for disclosure of at least a portion of the stored contextual information. Since the contextual information can be considered private, a user can desire for there to be regulations on divulging the information (e.g., when a user is unconscious, when a requestor is a paramedic, etc.). Thus, the user can use the identification component 306 to create or modify a policy used to regulate information disclosure. Selection can be facilitated through an established rule set (e.g., programmed by a user through a GUI), through at least one artificial intelligence technique, etc.

An artificial intelligence component 308 can be used to facilitate operation of aspects disclosed herein. For example, selection of the contextual information performed by the selection component 104 can be performed through use of at least one artificial intelligence technique. The artificial intelligence component 308 can employ one of numerous methodologies for learning from data and then drawing inferences and/or making determinations related to dynamically storing information across multiple storage units (e.g., Hidden Markov Models (HMMs) and related prototypical dependency models, more general probabilistic graphical models, such as Bayesian networks, e.g., created by structure search using a Bayesian model score or approximation, linear classifiers, such as support vector machines (SVMs), non-linear classifiers, such as methods referred to as "neural network" methodologies, fuzzy logic methodologies, and other approaches that perform data fusion, etc.) in accordance with implementing various automated aspects described herein. In addition, the artificial intelligence component 308 can also include methods for capture of logical relationships such as theorem provers or more heuristic rule-based expert systems. The artificial intelligence component 308 can be represented as an externally pluggable component, in some cases designed by a disparate (third) party.

Figure 4:
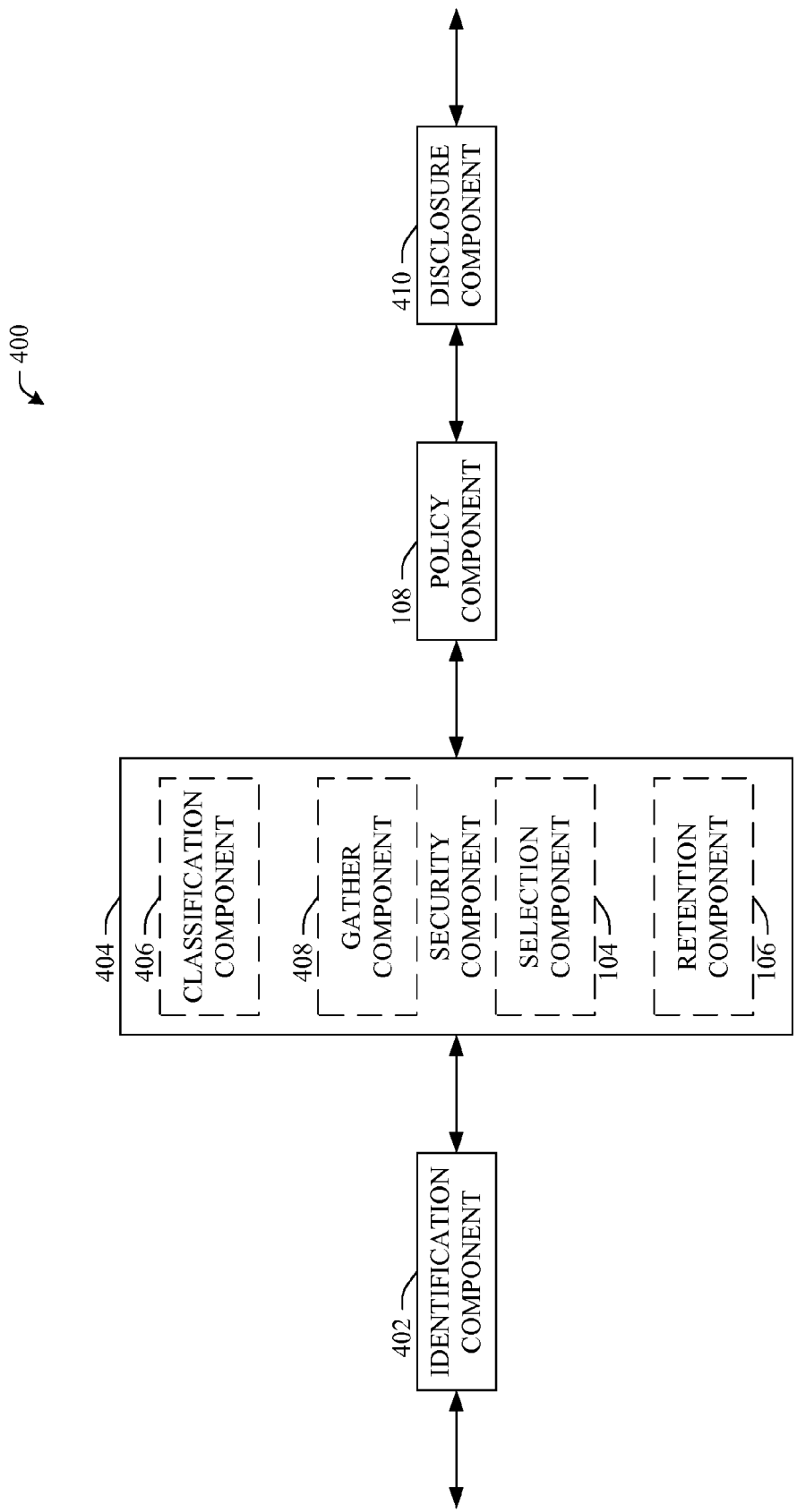
FIG. 4 illustrates a representative system for managing information retention in accordance with an aspect of the subject specification.

Now referring to FIG. 4, an example system 400 is provided for managing retention of contextual information. To conserve resources, contextual information can be gathered in limited instances, where the instances can be determined based upon surrounding circumstances (e.g., time of day). An identification component 402 can determine a situation beneficial regarding contextual information collection. The identification component 402 can function as means for identifying an instance when information should be collected.

A security component 404 can facilitate restricted retention of contextual information, commonly information that relates to a user. When the identification component 402 determines an instance for information collection, a classification component 406 can identify a type of data for collection. For instance, if a user is in an automobile accident, then the identification component 402 can determine that information should be collected and the classification component 406 can identify that brain wave information should be obtained. The classification component 406 can implement as means for identifying an instance when information should be collected. Additionally, the security component 404 can function as means for collecting the at least one criterion for disclosing the information retained upon the storage medium, the collected at least one criterion is identified and/or means for selecting the at least one criterion for disclosing the information retained upon the storage medium, the selected at least one criterion is identified and selection is performed through use at least one artificial intelligence technique.

A gather component 408 can obtain contextual information of a type designated by the classification component 406. In addition, the gather component 406 can obtain information directly submitted by a user. The gather component 406 can operate as means for obtaining contextual information of the classification that relates to an environment, user response information in relation to the environment, user contextual information that relates to the classification, and user input.

There can be storage size limitations, desirable efficiency marks, and the like that can encourage limited storing of contextual information. A selection component 104 can analyze collected information, determine information importance (e.g., relevancy, uniqueness compared to other stored information, etc.), and based upon the identified importance there can be choosing information for storage. The selection component 104 can operate as means for selecting at least a portion of the obtained contextual information, a portion of the obtained user input, a portion of the obtained user response information, or a combination thereof to be retained upon a storage medium. The storage medium can be a smart-card, non-volatile random access memory, etc.

A retention component 106 can store contextual information selected by the information designation component 102. According to one aspect, the retention component 106 analyzes available storage and determines an efficient manner to store the information. The retention component 106 can operate as means for retaining the selected information upon the storage medium in a hardware encrypted manner.

Based upon a set criteria (or criterion), a continuous attempt can be made to determine if the criteria are met. A policy component 110 can obtain relevant information, compare the information against the criteria, and make a decision if disclosure should occur. The policy component 110 can operate as means for identifying at least one criterion for disclosing the information retained upon the storage medium, the criterion is based upon a policy as well as means for determining if the at least one criterion is met. At least a portion of the retained information can be presented to an entity (e.g., person, computer, etc.) by a disclosure component 410. The disclosure component 410 can function as means for disclosing the information retained upon the storage medium through determination that the at least one criterion is met. According to one embodiment, the obtained contextual information relates to a physical state of the user, the user input relates to medical information of the user, and the at least one criterion for disclosing the information retained upon the storage medium is based upon the physical state of the user.

Figure 5:
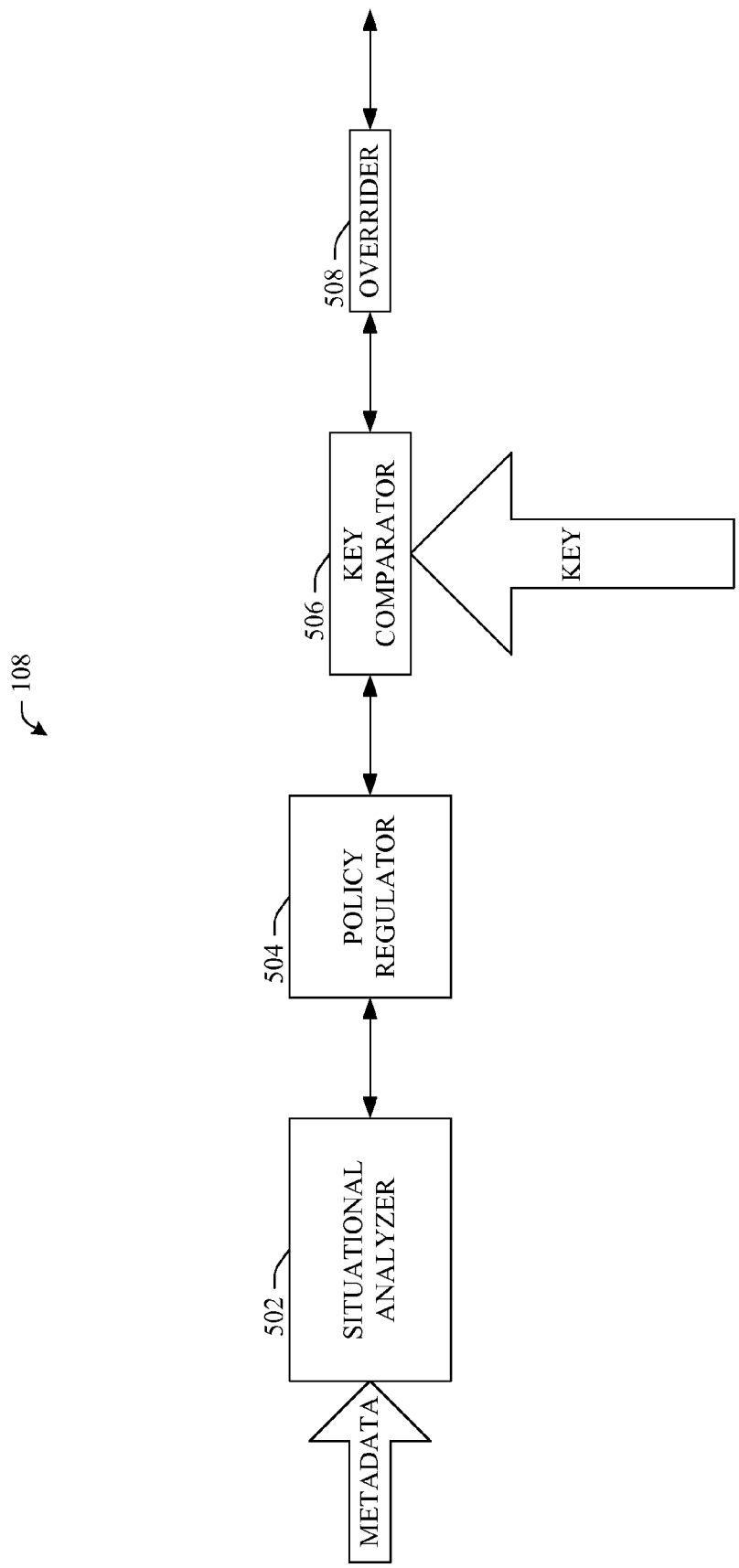
FIG. 5 illustrates a representative policy component in accordance with an aspect of the subject specification.

Now referring to FIG. 5, an example policy component 110 is provided for regulating information release. Information can be classified based upon importance and a situation analyzer 502 can determine if information should have regulated release (e.g., through a policy, through a key, etc.). For instance, the system 400 of FIG. 4 can retain velocity information as a user drives that is freely ascertainable—however, if the user is asked to stop by a police officer, the information can become subject to an access policy for a temporary time.

A policy can be used to determine an appropriate instance upon which to disclose information. A policy regulator 504 can be used to manage policies, including determine if a policy is met and alter policies when appropriate. For instance, a user can define a policy that medical information cannot be released to his spouse. However, if the user suffers from a serious injury and there is no one but his spouse nearby, then the policy regulator 504 can determine that the policy should be changed to allow for information in extreme circumstances. Additionally, policies can be modified and created by the policy regulator 504 through artificial intelligence techniques. According to one embodiment, the policy regulator 504 can operate as a filter component that can limit an amount of stored contextual information disclosed upon the policy component 110 determining access should be granted based upon the policy.

Access to information can be not only managed through a policy, but also through providing keys. A requester can provide a digital key and a key comparator 506 can determine if the requestor should be allowed based upon matching the provided key with an allowable key list. If an inappropriate key is provided (e.g., a key that does not match an entry on an approved key list), then the key comparator 506 can provide a rejection. However, if a proper key is provided, then the key comparator 506 can refer to the policy regulator 504 to determine if access should be granted. For instance, even if a proper key is provided, if a policy requires a user to be in a state that she is not in, then the policy component 110 can deny a request (e.g., a proper key is provided, but access is not granted unless a user is unconscious—therefore, access is denied).

Unexpected situations can arise upon which a user can desire that policies not be followed. For example, a policy can be created that a user does not want medical information to be released to anyone than a family physician. If the user is in an accident and paramedics arrive, then the user can desire for the policy not to be followed and the paramedics to gain access. An overrider 508 can be implemented to allow a user to override a policy and/or remove a requirement for a digital key. The overrider 508 can be applied to one policy or globally. In addition, the user can override certain aspects of a policy (e.g., lower a required number of keys for access from three to two) as well as a policy overall.

Figure 6:
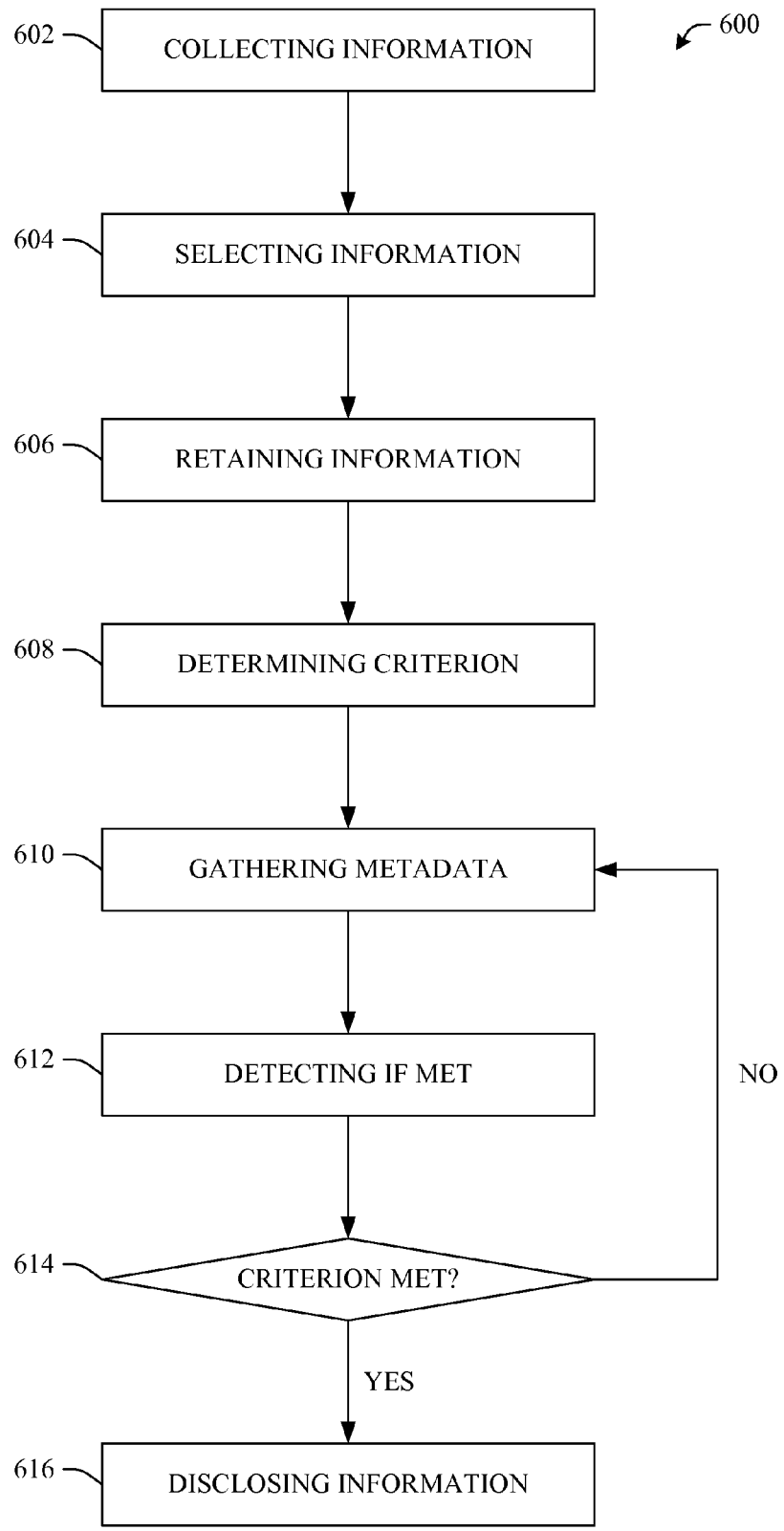
FIG. 6 illustrates a representative methodology for determining if securely retained information should be disclosed in accordance with an aspect of the subject specification.

Now referring to FIG. 6, an example methodology 600 is provided for determining if retained contextual information should be disclosed. At block 602, contextual information can be collected, commonly through employment of various sensors. An initial analysis of the information can occur to determine validity and/or accuracy of the information.

At least a portion of the collected contextual information can be selected for retention at event 604. Action 606 can include securely retaining at least a portion of the collected contextual information, commonly through information retention with hardware encryption. According to one embodiment, the collected contextual information relates to an environment or relates to an action of a user.

At act 608, there can be determining at least one criterion indicative of when retained contextual information of a user is to be released. For instance, a user or entity can specify at least one criterion and/or criterion can be inferred from historical operation. Metadata can be collected that relates to if the retained information should be released at act 610 and there can be detecting if the at least one criterion is met through event 612.

A check 614 can occur to determine if the criterion is met—for example, a comparison can be made of credentials of a requestor against desirable credentials for release. If the check 614 results in a negative response, then the methodology 600 can return to act 610 to collect more relevant metadata. However, if the check 614 determines criterion is met, then at least a portion of retained information can be disclosed at event 616. Event 616 can implement as releasing the retained contextual information upon detection of the at least one criterion being met, the criterion is based upon a role of a requesting individual, situational information, a user request, or a combination thereof. When retained contextual information is disclosed, a record of the information can be deleted, modified, make more secure, etc.

Figure 7:
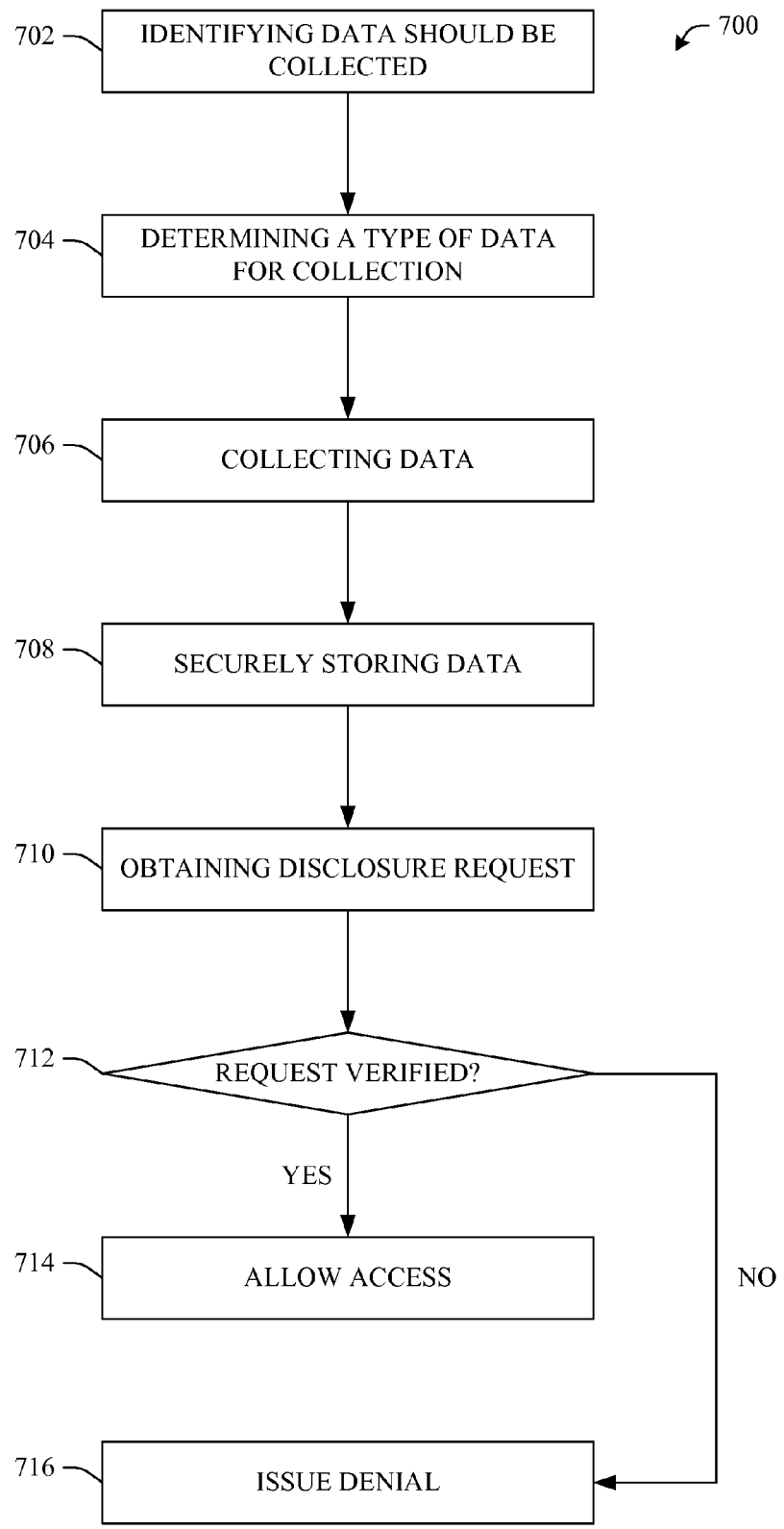
FIG. 7 illustrates a representative methodology for processing a disclosure request in accordance with an aspect of the subject specification.

Now referring to FIG. 7, an example methodology 700 is provided for processing a disclosure request. Identification can take place to determine that contextual data should be retained at event 702. However, collection of virtually all available contextual information can be cumbersome, so specific types of information for collection can be designated at action 704.

A designated type of contextual information can be collected through act 706 and securely retained at event 708, commonly through implementation of hardware encryption. A request to disclose the securely retained information can be collected and processed at act 710. Based upon the analysis, a verification check 712 can take place to determine if information should be disclosed to a requesting entity. For example, a paramedic can request contextual information and a message can be sent to a personal device of a user. If the user accepts the message, then there can be verification; if the user denies or ignores the message, then there can be a failure of verification. If a request is verified, then access can be granted at event 714; if the request is not verified, then access can be denied at act 716.

Figure 8:
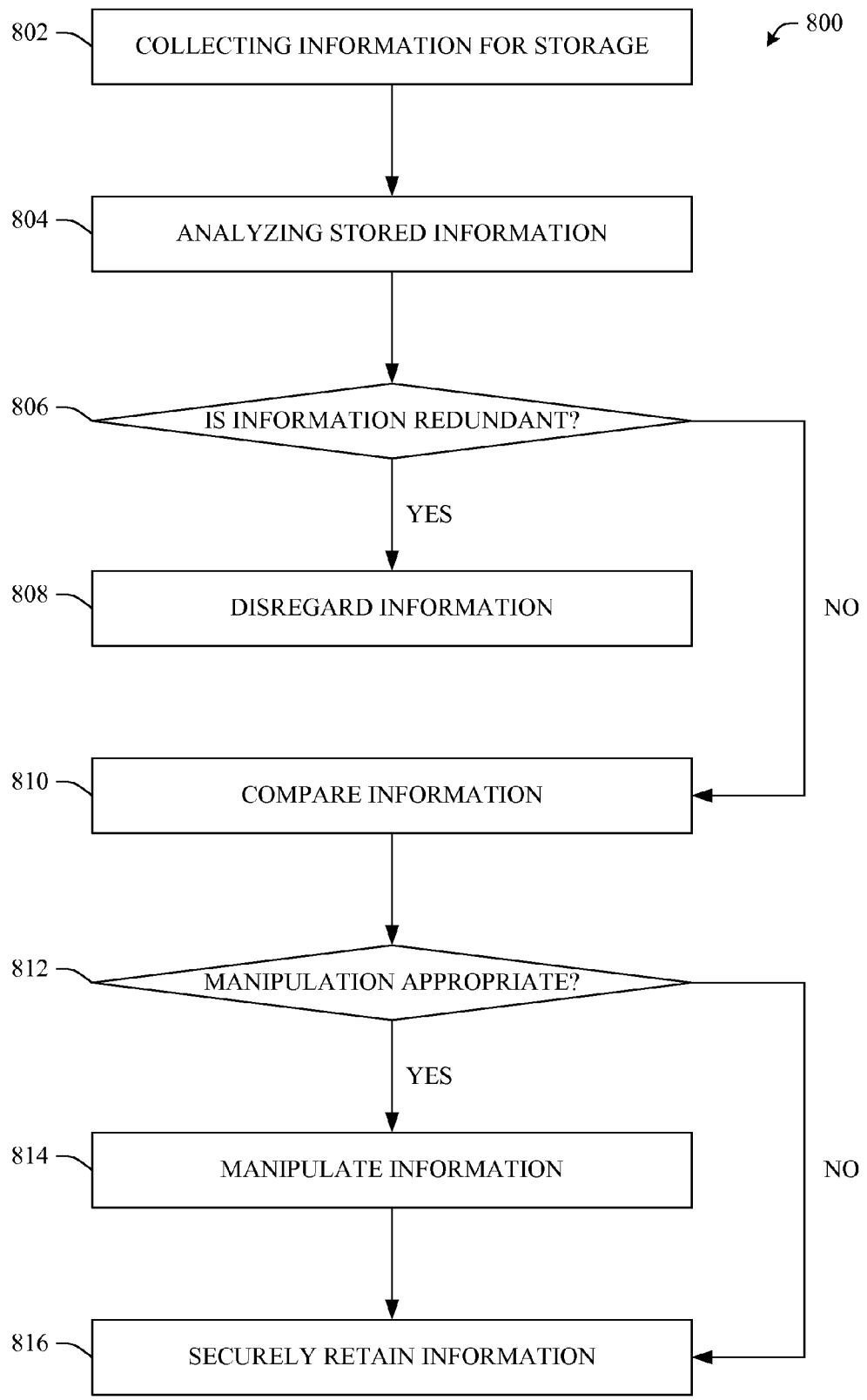
FIG. 8 illustrates a representative methodology for manipulating information concerning secure storage in accordance with an aspect of the subject specification.

Now referring to FIG. 8, an example methodology 800 is provided for performing manipulation of information in regard to secure and efficient storage. Contextual information can be collected and evaluated at event 802 and information retained upon a designated storage medium can be analyzed at action 804. A check 806 can determine if there is exact redundancy between collected information and retained information. If there is exact redundancy, then the collected information can be disregarded at act 808.

The collected information can be compared against information retained at event 810 if there is not exact redundancy and check 812 can function determine if there is a level of redundancy and/or if manipulation of information (e.g., stored information, collected information, etc.) is appropriate. If manipulation is appropriate, then manipulation can be performed at act 814. For instance, about ten heart rate monitor readings can take place, where there is a high of about 88 beats per minute as a low and about 82 beats per minute as a high. As opposed to retaining ten records, manipulation can take place averaging monitor values and specifying a high and low value with a number of monitored instances. If there is no redundancy and/or information is not likely to benefit from manipulation, then the collected information can be retained at event 816.

Figure 9:
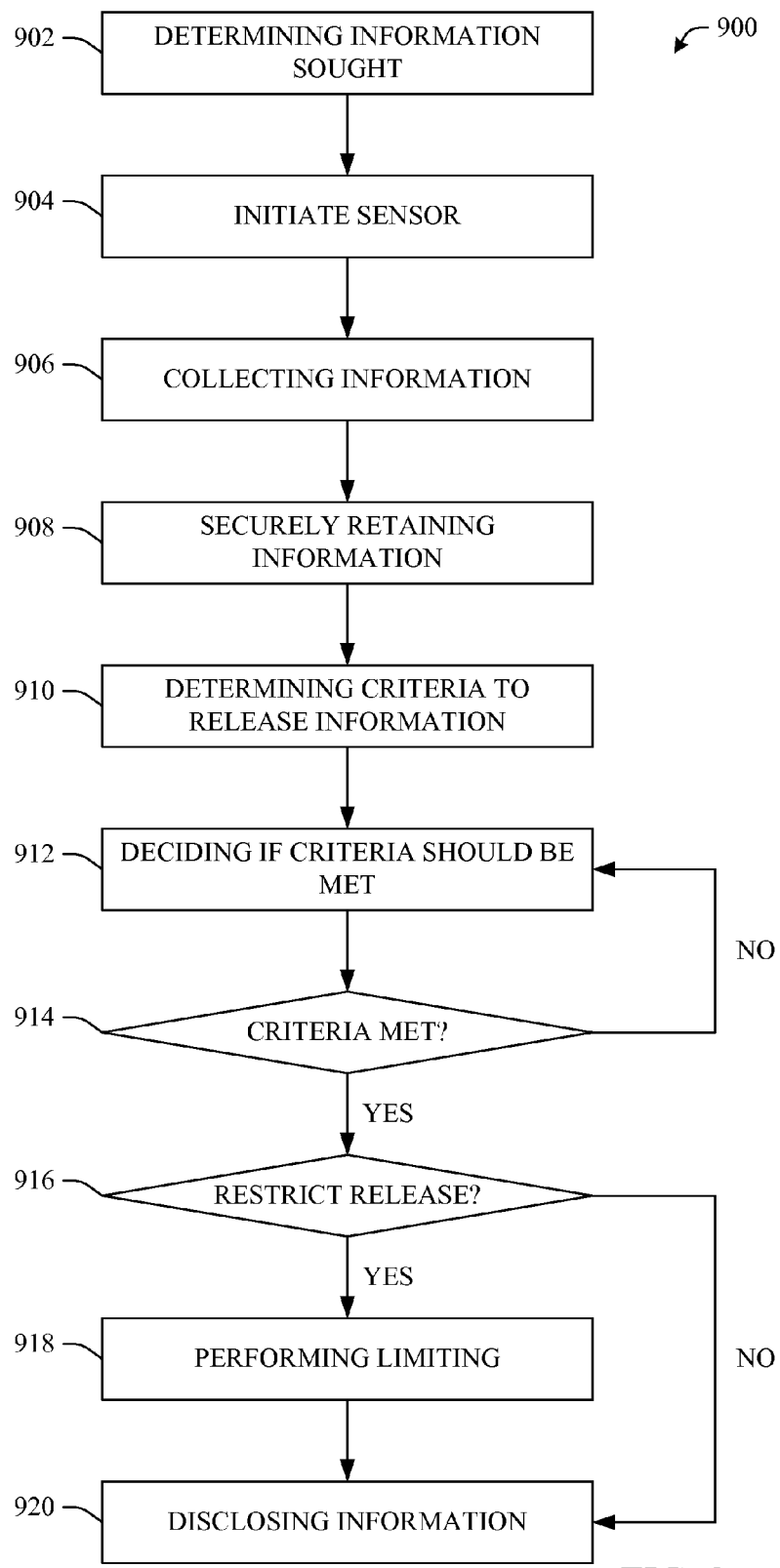
FIG. 9 illustrates a representative methodology for determining if information for release should be restricted in accordance with an aspect of the subject specification.

Now referring to FIG. 9, an example methodology 900 is provided for regulating information disclosure. A classification of information sought can be determined at action 902 and based upon the determination a particular type of sensor designed to gather the class of information could be initiated at event 904. Information from the sensor can be collected at act 906 and securely retained (e.g., through hardware encryption) at event 908.

There can be determining at least one criterion indicative of when retained contextual information of a user should be released at act 910. Appropriate metadata can be collected and there can be detecting if the at least one criterion is met at event 912. Thought check 914, if a standard is not met, then the methodology 900 can return to event 912 to collect more metadata and determine if the standard is met.

If the standard is met, then check 916 can determine if a restricted release of information is appropriate. For instance, a contextual information collection device can retain information related to various aspects of a user's life (e.g., financial, medical, marital, and the like). If the user suffers from a medical condition, a paramedic can find it necessary to obtain user medical information. However, the user may not want the paramedic to view financial information and therefore it can be appropriate to restrict information. In addition to class, specific information can be withheld. For instance, the paramedic can receive recent heart information; however, toe surgery information can be withheld since it could be irrelevant and/or potentially embarrassing. Therefore, if there is to be limited disclosure, then appropriate restrictions of information can occur at action 918. In addition, limitations in information use can occur, such as allowing information to be read upon a personal electronic device, but banning copying of the information to an unknown storage medium. At act 920, retained contextual information can be disclosed (e.g., limited through action 918, directly as a result of the check 916 determining there should be no restriction, and the like).

Figure 10:
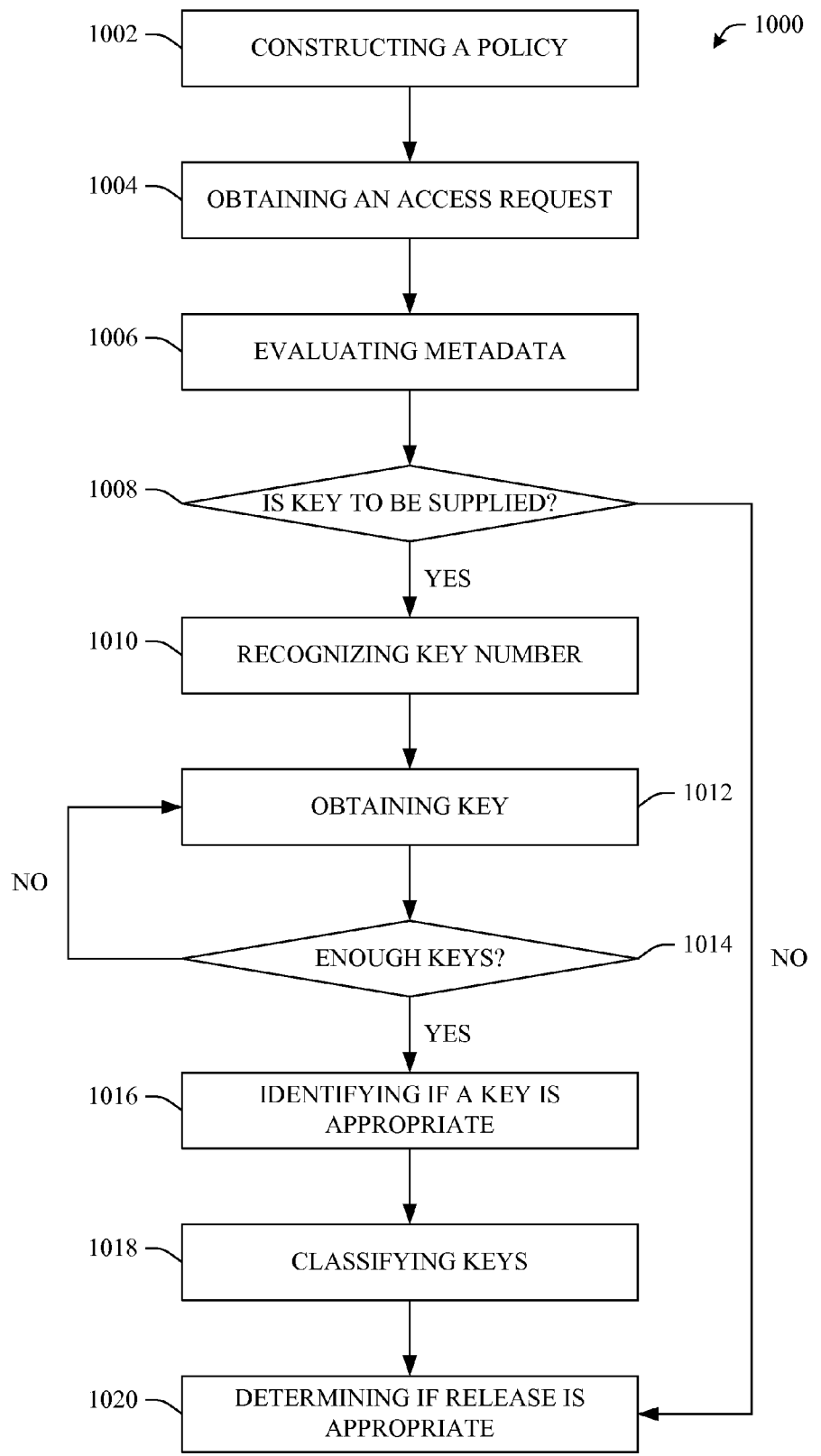
FIG. 10 illustrates a representative methodology for regulating information release in accordance with an aspect of the subject specification.

Now referring to FIG. 10, an example methodology 1000 is provided for determining if retained information (e.g., information retained in a hardware encrypted manner) should be disclosed via use of a policy. A policy can be constructed through action 1002. Construction of the policy can occur through user instruction, artificial intelligence techniques, by a third party, and the like.

A request can be obtained to access the retained information through event 1004. Metadata related to the request can be collected and evaluated at act 1006. Act 1006 can include evaluating metadata in relation to a policy that governs releasing information retained through a processor and a persistent memory type. In addition to using a policy to regulate data release, a digital key can also be used.

Therefore, a check 1008 can be performed if a digital key is to be supplied in conjunction with determinations made through the policy. If it is determined that keys are to be used, then a number of keys for use can be recognized at action 1010. For example, at least one of three keys can be required for disclosure of information—thus there is recognition of one required key out of three potential keys. Appropriate keys can be obtained at action 1012 and a check 1014 can determine if enough keys are supplied. If enough keys are not supplied (e.g., one key is supplied when two are required), then the methodology 1000 can return to action 1012. However, in an alternate embodiment, the methodology can deny access if enough keys are not provided.

If enough keys are provided, then action 1016 can be identifying if a provided key matches at least one entry of an approved key list. There can be classifying a number of keys provided at event 1018. For example, five keys can be provided, but only two match with an entry—event 1018 can compare the approved keys against a required number of keys. If only two are required, then the methodology 1000 can continue while the methodology 1000 can terminate (e.g., access can be denied) if there are not enough keys. If there are enough keys, keys do not need to be supplied, and the like, then action 1020 can allow for determining if the information should be released as a function of a result of the evaluation (e.g., is the policy met).

For purposes of simplicity of explanation, methodologies described above can be implemented in accordance with the disclosed subject matter were shown and described as a series of blocks. However, it is to be understood and appreciated that the claimed subject matter is not limited by the order of the blocks, as some blocks can occur in different orders and/or concurrently with other blocks from what is depicted and described herein. Moreover, not all illustrated blocks can be required to implement the methodologies described hereinafter. Additionally, it should be further appreciated that the methodologies disclosed throughout this specification are capable of being stored on an article of manufacture to facilitate transporting and transferring such methodologies to computers. The term article of manufacture, as used, is intended to encompass a computer program accessible from any computer-readable device, carrier, or media. Additionally, it is to be appreciated that determinations and/or inferences discussed in the subject specification can be practiced through use of artificial intelligence techniques.

Figure 11:
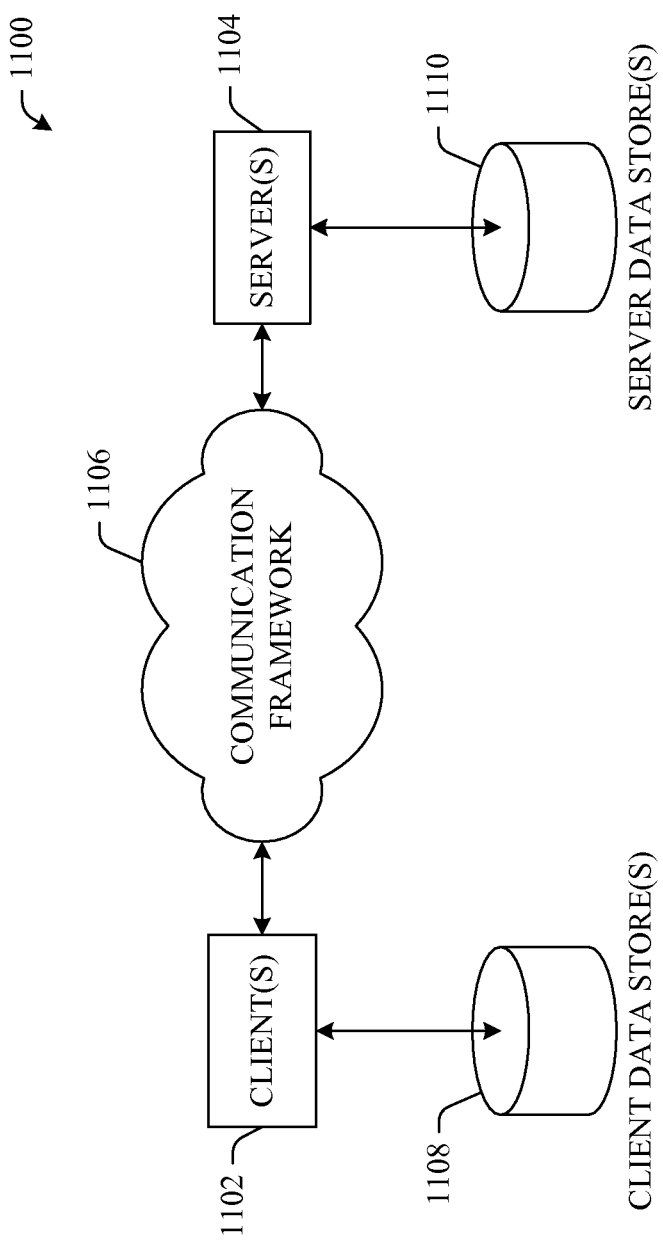
FIG. 11 illustrates an example of a schematic block diagram of a computing environment in accordance with an aspect subject specification.
Figure 12:
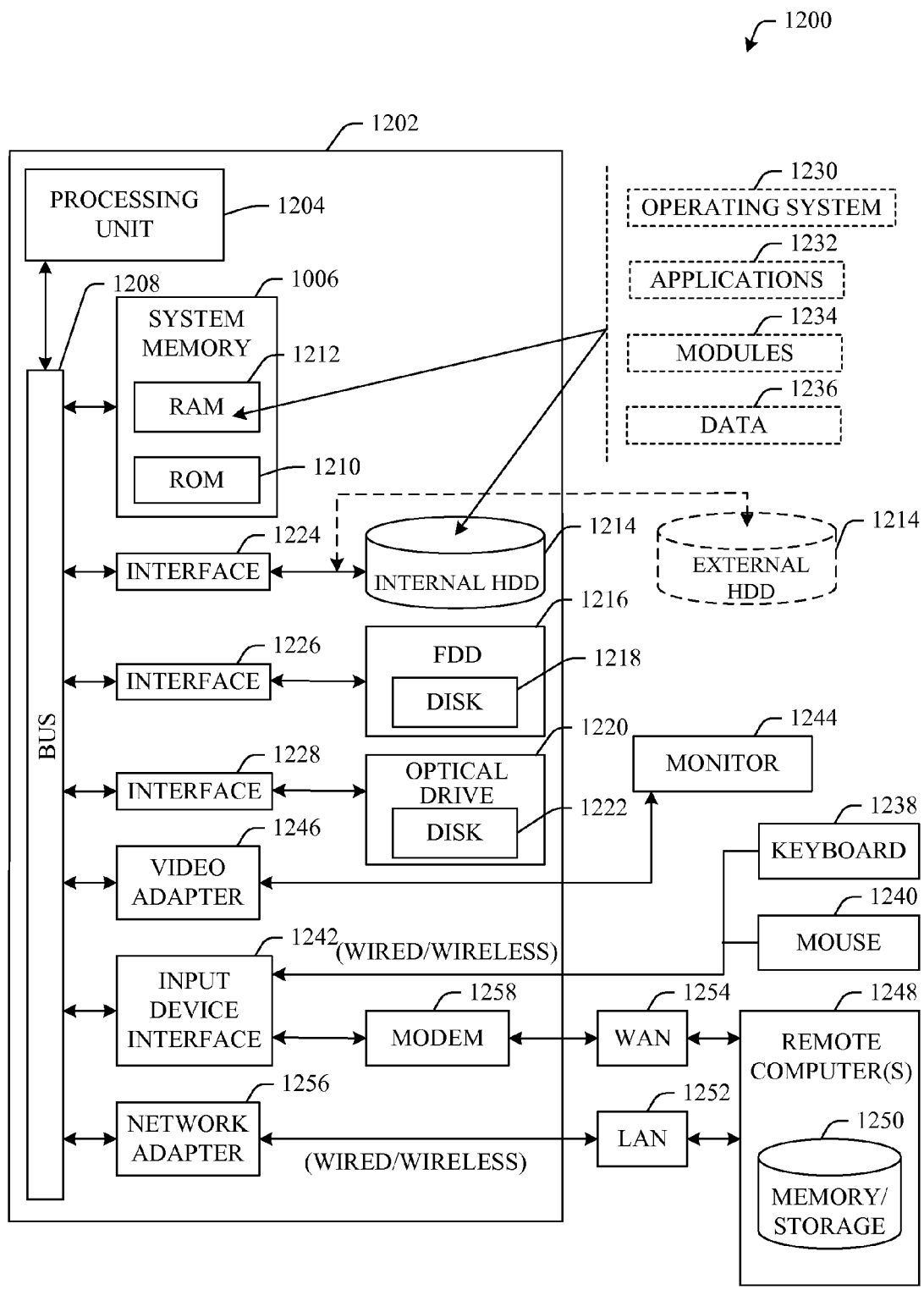
FIG. 12 illustrates an example of a block diagram of a computer operable to execute the disclosed architecture.

In order to provide a context for the various aspects of the disclosed subject matter, FIGS. 11 and 12 as well as the following discussion are intended to provide a brief, general description of a suitable environment in which the various aspects of the disclosed subject matter can be implemented. While the subject matter has been described above in the general context of computer-executable instructions of a program that runs on one or more computers, those skilled in the art will recognize that the subject matter described herein also can be implemented in combination with other program modules. Generally, program modules include routines, programs, components, data structures, etc. that perform particular tasks and/or implement particular abstract data types. Moreover, those skilled in the art will appreciate that the inventive methods can be practiced with other computer system configurations, including single-processor, multiprocessor or multi-core processor computer systems, mini-computing devices, mainframe computers, as well as personal computers, hand-held computing devices (e.g., personal digital assistant (PDA), phone, watch . . . ), microprocessor-based or programmable consumer or industrial electronics, and the like. The illustrated aspects can also be practiced in distributed computing environments where tasks are performed by remote processing devices that are linked through a communications network. However, some, if not all aspects of the claimed subject matter can be practiced on stand-alone computers. In a distributed computing environment, program modules can be located in both local and remote memory storage devices.

Referring now to FIG. 11, there is illustrated a schematic block diagram of a computing environment 1100 in accordance with the subject specification. The system 1100 includes one or more client(s) 1102. The client(s) 1102 can be hardware and/or software (e.g., threads, processes, computing devices). The client(s) 1102 can house cookie(s) and/or associated contextual information by employing the specification, for example.

The system 1100 also includes one or more server(s) 1104. The server(s) 1104 can also be hardware and/or software (e.g., threads, processes, computing devices). The servers 1104 can house threads to perform transformations by employing the specification, for example. One possible communication between a client 1102 and a server 1104 can be in the form of a data packet adapted to be transmitted between two or more computer processes. The data packet can include a cookie and/or associated contextual information, for example. The system 1100 includes a communication framework 1106 (e.g., a global communication network such as the Internet) that can be employed to facilitate communications between the client(s) 1102 and the server(s) 1104.

Communications can be facilitated via a wired (including optical fiber) and/or wireless technology. The client(s) 1102 are operatively connected to one or more client data store(s) 1108 that can be employed to store information local to the client(s) 1102 (e.g., cookie(s) and/or associated contextual information). Similarly, the server(s) 1104 are operatively connected to one or more server data store(s) 1110 that can be employed to store information local to the servers 1104.

Referring now to FIG. 12, there is illustrated a block diagram of a computer operable to execute the disclosed architecture. In order to provide additional context for various aspects of the subject specification, FIG. 12 and the following discussion are intended to provide a brief, general description of a suitable computing environment 1200 in which the various aspects of the specification can be implemented. While the specification has been described above in the general context of computer-executable instructions that can run on one or more computers, those skilled in the art will recognize that the specification also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the specification can also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embody computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared and other wireless media. Combinations of the any of the above should also be included within the scope of computer-readable media.

With reference again to FIG. 12, the example environment 1200 for implementing various aspects of the specification includes a computer 1202, the computer 1202 including a processing unit 1204, a system memory 1206 and a system bus 1208. The system bus 1208 couples system components including, but not limited to, the system memory 1206 to the processing unit 1204. The processing unit 1204 can be any of various commercially available processors or proprietary specific configured processors. Dual microprocessors and other multi-processor architectures can also be employed as the processing unit 1204.

The system bus 1208 can be any of several types of bus structure that can further interconnect to a memory bus (with or without a memory controller), a peripheral bus, and a local bus using any of a variety of commercially available bus architectures. The system memory 1206 includes read-only memory (ROM) 1210 and random access memory (RAM) 1212. A basic input/output system (BIOS) is stored in a non-volatile memory 1210 such as ROM, EPROM, EEPROM, which BIOS contains the basic routines that help to transfer information between elements within the computer 1202, such as during start-up. The RAM 1212 can also include a high-speed RAM such as static RAM for caching data.

The computer 1202 further includes an internal hard disk drive (HDD) 1214 (e.g., EIDE, SATA), which internal hard disk drive 1214 can also be configured for external use in a suitable chassis (not shown), a magnetic floppy disk drive (FDD) 1216, (e.g., to read from or write to a removable diskette 1218) and an optical disk drive 1220, (e.g., reading a CD-ROM disk 1222 or, to read from or write to other high capacity optical media such as the DVD). The hard disk drive 1214, magnetic disk drive 1216 and optical disk drive 1220 can be connected to the system bus 1208 by a hard disk drive interface 1224, a magnetic disk drive interface 1226 and an optical drive interface 1228, respectively. The interface 1224 for external drive implementations includes at least one or both of Universal Serial Bus (USB) and IEEE 1394 interface technologies. Other external drive connection technologies are within contemplation of the subject specification.

The drives and their associated computer-readable media provide nonvolatile storage of data, data structures, computer-executable instructions, and so forth. For the computer 1202, the drives and media accommodate the storage of any data in a suitable digital format. Although the description of computer-readable media above refers to HDD, a removable magnetic diskette, and a removable optical media such as a CD or DVD, it should be appreciated by those skilled in the art that other types of media that are readable by a computer, such as zip drives, magnetic cassettes, flash memory cards, cartridges, and the like, can also be used in the example operating environment, and further, that any such media can contain computer-executable instructions for performing the methods of the specification.

A number of program modules can be stored in the drives and RAM 1212, including an operating system 1230, one or more application programs 1232, other program modules 1234 and program data 1236. All or portions of the operating system, applications, modules, and/or data can also be cached in the RAM 1212. It is appreciated that the specification can be implemented with various proprietary or commercially available operating systems or combinations of operating systems.

A user can enter commands and information into the computer 1202 through one or more wired/wireless input devices, e.g., a keyboard 1238 and a pointing device, such as a mouse 1240. Other input devices (not shown) can include a microphone, an IR remote control, a joystick, a game pad, a stylus pen, touch screen, or the like. These and other input devices are often connected to the processing unit 1204 through an input device interface 1242 that is coupled to the system bus 1208, but can be connected by other interfaces, such as a parallel port, an IEEE 1394 serial port, a game port, a USB port, an IR interface, etc.

A monitor 1244 or other type of display device is also connected to the system bus 1208 via an interface, such as a video adapter 1246. In addition to the monitor 1244, a computer typically includes other peripheral output devices (not shown), such as speakers, printers, etc.

The computer 1202 can operate in a networked environment using logical connections via wired and/or wireless communications to one or more remote computers, such as a remote computer(s) 1248. The remote computer(s) 1248 can be a workstation, a server computer, a router, a personal computer, portable computer, microprocessor-based entertainment appliance, a peer device or other common network node, and typically includes many or all of the elements described relative to the computer 1202, although, for purposes of brevity, only a memory/storage device 1250 is illustrated. The logical connections depicted include wired/wireless connectivity to a local area network (LAN) 1252 and/or larger networks, e.g., a wide area network (WAN) 1254. Such LAN and WAN networking environments are commonplace in offices and companies, and facilitate enterprise-wide computer networks, such as intranets, all of which can connect to a global communications network, e.g., the Internet.

When used in a LAN networking environment, the computer 1202 is connected to the local network 1252 through a wired and/or wireless communication network interface or adapter 1256. The adapter 1256 can facilitate wired or wireless communication to the LAN 1252, which can also include a wireless access point disposed thereon for communicating with the wireless adapter 1256.

When used in a WAN networking environment, the computer 1202 can include a modem 1258, or is connected to a communications server on the WAN 1254, or has other means for establishing communications over the WAN 1254, such as by way of the Internet. The modem 1258, which can be internal or external and a wired or wireless device, is connected to the system bus 1208 via the input device interface 1242. In a networked environment, program modules depicted relative to the computer 1202, or portions thereof, can be stored in the remote memory/storage device 1250. It will be appreciated that the network connections shown are example and other means of establishing a communications link between the computers can be used.

The computer 1202 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

The aforementioned systems have been described with respect to interaction among several components. It should be appreciated that such systems and components can include those components or sub-components specified therein, some of the specified components or sub-components, and/or additional components. Sub-components can also be implemented as components communicatively coupled to other components rather than included within parent components. Additionally, it should be noted that one or more components could be combined into a single component providing aggregate functionality. The components could also interact with one or more other components not specifically described herein but known by those of skill in the art.

As used herein, the terms to "infer" or "inference" refer generally to the process of reasoning about or deducing states of the system, environment, and/or user from a set of observations as captured via events and/or data. Inference can be employed to identify a specific context or action, or can generate a probability distribution over states, for example.

The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

Furthermore, the claimed subject matter can be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications can be made to this configuration without departing from the scope or spirit of the claimed subject matter.

Moreover, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to disclose concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What has been described above includes examples of the subject specification. It is, of course, not possible to describe every conceivable combination of components or methodologies for purposes of describing the subject specification, but one of ordinary skill in the art can recognize that many further combinations and permutations of the subject specification are possible. Accordingly, the subject specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A data storage system for creating and utilizing access policies for stored information related to a user, the system comprising:
    an identification component, utilizing one or more processors, to create the access policies based at least in part on one or more conditions including at least one of a current state of the user, a current environment of the user, or specific information withheld by the user;
    a communication component, utilizing a communication network, to obtain an override request from the user, the override request indicating a requisite number of digital keys to apply to an access policy of the access policies;
    an overrider component, utilizing the one or more processors, to change the access policy of the access policies to indicate the requisite number of digital keys in response to obtaining the override request from the user;
    the communication component, utilizing the communication network, to obtain a request from a requestor to view the stored information, the request including one or more valid keys;
    a policy component, utilizing the communication network, to regulate access to the stored information in response to the request and based at least in part upon a particular access policy that corresponds to the one or more conditions present at a time of obtaining the request, the policy component to deny access in response to determining that a count of the one or more valid keys included in the request is fewer than the requisite number of digital keys; and
    the policy component to generate a response including at least one of granting access to at least a portion of the stored information or requesting more information from the requestor.

2. The system of claim 1, further comprising: a graphical user interface (GUI) for the user to modify the access policies.

3. The system of claim 1, wherein the identification component creates a new access policy based on at least one of the digital keys and the current state of the user.

4. The system of claim 1, wherein the policy component generates the response by:
    granting access to the requestor based in part on the user being in a first current state;
    denying access to the requestor based in part on the user being in a second current state; and
    partially granting access and partially denying access to the stored information based in part on the user being in a third current state.

5. The system of claim 1, wherein the requisite number of digital keys specified by the access policy is based at least in part upon a type of data requested by the requestor.

6. The system of claim 1 further comprising, a management component to:
    aggregate repetitive information utilizing the one or more processors;
    disregard collected information redundant with the stored information;
    delete a part of the stored information based at least in part on an age of the part of the stored information; and
    in response to determining that the response includes granting access to the information, utilizing the one or more processors, prioritize an order that the information is disclosed to the requestor.

7. A method of retaining information and storing the information on a storage device utilizing a processor, the method comprising:
    gathering a continuous record of contextual information relating to a user, environmental information, and a response of the user to an environment;
    selecting a portion of the contextual information for storing by determining whether measurements of the contextual information are within a tolerance, wherein one or more portions of the contextual information associated with the measurements within the tolerance are selected and one or more disregarded portions of the contextual information associated with the measurements outside of the tolerance are disregarded;

storing the one or more selected portions of the contextual information to the storage device;

creating an access policy based at least partly on the contextual information, the access policy including at least a key and a current state of the user; and obtaining, using a communication network, an override request from the user, the override request indicating a requisite number of digital keys to apply to the access policy.

8. The method of claim 7, further comprising modifying the gathering of the contextual information based at least in part upon a user selection or automatic starting, stopping, or deleting of the contextual information.

9. The method of claim 7, further comprising determining whether the contextual information is accurate, and in response to the contextual information being inaccurate, gathering a second contextual information.

10. The method of claim 9, wherein determining whether the contextual information is accurate further comprises gathering the contextual information multiple times and determining whether the contextual information gathered at the multiple times matches within the tolerance.

11. The method of claim 7, further comprising:
identifying, utilizing the one or more processors, a discrepancy between two or more values for an identified portion of the contextual information;
calculating, utilizing the one or more processors, an expected value for the portion of the contextual information; and
storing, to a memory, at least one of the two or more values for the portion of the contextual information that is closest to the expected value.

12. The method of claim 7, further comprising:
determining, utilizing one or more sensors, the current state of the user; and
based at least in part on the current state of the user, stopping the gathering of a first type of contextual information and increasing a rate of gathering a second type of contextual information.

13. The method of claim 7, further comprising:
determining, utilizing one or more sensors, the current state of the user;
based at least in part on the current state of the user, identifying a second type of contextual information to gather; and
gathering the type of the contextual information.

14. The method of claim 7, further comprising managing the contextual information, the managing including:
aggregating, utilizing the one or more processors, repetitive contextual information; and
deleting, from a memory, the repetitive contextual information based at least in part on an age of the contextual information.

15. The method of claim 7, wherein the selecting the portion of the contextual information is based at least in part upon a uniqueness of the contextual information.

16. The method of claim 7, wherein the selecting the portion of the contextual information is based at least in part upon an available storage size of the storage device and an optimal operating efficiency of the storage device.

17. The method of claim 7, further comprising:
determining, utilizing the one or more processors, a level of redundancy between the contextual information and the portion of the contextual information;
in response to determining that the level of redundancy is above a first level, disregarding the contextual information;
in response to determining that the level of redundancy is below the first level and above a second level, storing, to the storage device, average, high and low values of the contextual information and a number of instances of the contextual information from a memory;
in response to determining that the level of redundancy is below the second level, storing, to the storage device, the contextual information from the memory.

18. The method of claim 7, wherein the environmental information includes at least one of: a decibel level in a room or a number of people in the room.

19. The method of claim 7, wherein the response of the user to the environment includes at least one of a change in a level of stress of the user or a level of perspiration of the user.

20. One or more computer-readable storage devices containing instructions that, when executed by one or more processors, cause the one or more processors to perform acts comprising:
gathering a continuous record of contextual information relating to a user, the contextual information including location information, environmental information, a response of the user to an environment, an input of the user, and actions of the user;
creating an access policy based at least in part on the contextual information, the contextual information including at least a key and current state of the user;
obtaining, using a communication network, an override request from the user, the override request indicating a requisite number of digital keys to apply to the access policy;
changing the requisite number of digital keys specified by the access policy in response to a change to at least one of the key or the current state of the user;
obtaining a request from a requestor to view information utilizing the communication network, the request including one or more valid keys;
determining whether to release the stored information to the requestor based at least in part upon the access policy that corresponds to one or more existing conditions present at a time of the request, the determining based, at least in part, on whether the one or more valid keys equals or exceeds the requisite number of digital keys; and
generating a response for the requestor, including at least one of granting access to at least a portion of the stored information or requesting more information from the requestor.

* * * * *